(12) United States Patent
Wang et al.

(10) Patent No.: US 8,983,174 B2
(45) Date of Patent: Mar. 17, 2015

(54) MOBILE ROBOT WITH A HEAD-BASED MOVEMENT MAPPING SCHEME

(71) Applicants: Yulun Wang, Goleta, CA (US); Charles S. Jordan, Santa Barbara, CA (US); Keith P. Laby, Santa Barbara, CA (US); Jonathan Southard, Santa Barbara, CA (US); Marco Pinter, Santa Barbara, CA (US); Brian Miller, Santa Barbara, CA (US)

(72) Inventors: Yulun Wang, Goleta, CA (US); Charles S. Jordan, Santa Barbara, CA (US); Keith P. Laby, Santa Barbara, CA (US); Jonathan Southard, Santa Barbara, CA (US); Marco Pinter, Santa Barbara, CA (US); Brian Miller, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 200 days.

(21) Appl. No.: 13/770,138

(22) Filed: Feb. 19, 2013

(65) Prior Publication Data

US 2013/0155221 A1 Jun. 20, 2013

Related U.S. Application Data

(63) Continuation of application No. 12/413,038, filed on Mar. 27, 2009, now Pat. No. 8,401,275.

(51) Int. Cl.
| | |
|---|---|
| *G06K 9/00* | (2006.01) |
| *G06F 3/033* | (2013.01) |
| *A61B 19/00* | (2006.01) |
| *B25J 5/00* | (2006.01) |
| *B25J 13/02* | (2006.01) |

(Continued)

(52) U.S. Cl.
CPC ............... *G06F 3/033* (2013.01); *A61B 19/22* (2013.01); *B25J 5/007* (2013.01); *B25J 13/02* (2013.01); *B25J 19/023* (2013.01); *G05D 1/0038* (2013.01); *A61B 19/2203* (2013.01); *Y10S 901/01* (2013.01); *G05D 2201/0206* (2013.01)
USPC ................................ 382/153; 700/245; 901/1

(58) Field of Classification Search
USPC ................................ 382/153; 901/8; 700/245
See application file for complete search history.

(56) References Cited

U.S. PATENT DOCUMENTS

| | | | |
|---|---|---|---|
| 3,821,995 | A | 7/1974 | Aghnides |
| 4,107,689 | A | 8/1978 | Jellinek |

(Continued)

FOREIGN PATENT DOCUMENTS

| | | |
|---|---|---|
| AU | 1216200 A | 5/2000 |
| CA | 2289697 A1 | 11/1998 |

(Continued)

OTHER PUBLICATIONS

"Robart I, II, III", Spawar, Systems Center Pacific, Available online at <http://www.nosc.mil/robots/land/robart/robart.html>, retrieved on Nov. 22, 2010, 1998, 8 pages.

(Continued)

*Primary Examiner* — John Strege
(74) *Attorney, Agent, or Firm* — Chris Lambrecht

(57) ABSTRACT

A robotic system that includes a mobile robot and a remote input device. The input device may be a joystick that is used to move a camera and a mobile platform of the robot. The system may operate in a mode where the mobile platform moves in a camera reference coordinate system. The camera reference coordinate system is fixed to a viewing image provided by the camera so that movement of the robot corresponds to a direction viewed on a screen. This prevents disorientation during movement of the robot if the camera is panned across a viewing area.

22 Claims, 8 Drawing Sheets

(51) Int. Cl.
 *B25J 19/02* (2006.01)
 *G05D 1/00* (2006.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |

(56) References Cited

U.S. PATENT DOCUMENTS

| | | |
|---|---|---|
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,317,652 B1 | 11/2001 | Osada |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |

(56) References Cited

U.S. PATENT DOCUMENTS

| | | |
|---|---|---|
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,643,051 B2 | 1/2010 | Sandberg et al. |
| 7,647,320 B2 | 1/2010 | Mok et al. |
| 7,680,038 B1 | 3/2010 | Gourlay |
| 7,693,757 B2 | 4/2010 | Zimmerman |
| 7,698,432 B2 | 4/2010 | Short et al. |
| 7,719,229 B2 | 5/2010 | Kaneko et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,463,435 B2 | 6/2013 | Herzog et al. |
| 8,503,340 B1 | 8/2013 | Xu |
| 8,527,094 B2 | 9/2013 | Kumar et al. |
| 8,532,860 B2 | 9/2013 | Daly |
| 8,726,454 B2 | 5/2014 | Gilbert, Jr. et al. |
| 2001/0002448 A1 | 5/2001 | Wilson et al. |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0111988 A1 | 8/2002 | Sato |
| 2002/0120362 A1 | 8/2002 | Lathan et al. |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0199000 A1 | 10/2003 | Valkirs et al. |
| 2003/0206242 A1 | 11/2003 | Choi |
| 2003/0212472 A1 | 11/2003 | McKee |
| 2003/0216833 A1 | 11/2003 | Mukai et al. |
| 2003/0216834 A1 | 11/2003 | Allard |

(56) References Cited

U.S. PATENT DOCUMENTS

| | | |
|---|---|---|
| 2003/0220541 A1 | 11/2003 | Salisbury, Jr. et al. |
| 2003/0220715 A1 | 11/2003 | Kneifel, II et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125098 A1 | 6/2005 | Wang et al. |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0267826 A1 | 12/2005 | Levy et al. |
| 2005/0283414 A1 | 12/2005 | Fernandes et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0064212 A1 | 3/2006 | Thorne |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandberg et al. |
| 2007/0078566 A1 | 4/2007 | Wang et al. |

(56) References Cited

U.S. PATENT DOCUMENTS

| | | |
|---|---|---|
| 2007/0112700 A1 | 5/2007 | Den Haan et al. |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0126132 A1 | 5/2008 | Warner et al. |
| 2008/0133052 A1 | 6/2008 | Jones et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0255703 A1 | 10/2008 | Wang et al. |
| 2008/0263451 A1 | 10/2008 | Portele et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0286905 A1 | 11/2010 | Goncalves et al. |
| 2010/0323783 A1 | 12/2010 | Nonaka et al. |
| 2011/0050841 A1 | 3/2011 | Wang et al. |
| 2011/0071702 A1 | 3/2011 | Wang et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0191246 A1 | 7/2012 | Roe et al. |
| 2012/0191464 A1 | 7/2012 | Stuart et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| GB | 2431261 A | 4/2007 |
| JP | 07-194609 A | 8/1995 |
| JP | 7-213753 A | 8/1995 |
| JP | 7-248423 A | 9/1995 |
| JP | 7-257422 A | 10/1995 |
| JP | 8-84328 A | 3/1996 |
| JP | 8-320727 A | 12/1996 |
| JP | 9-267276 A | 10/1997 |
| JP | 10-79097 A | 3/1998 |

(56) References Cited

FOREIGN PATENT DOCUMENTS

| | | |
|---|---|---|
| JP | 10-288689 A | 10/1998 |
| JP | 11-220706 A | 8/1999 |
| JP | 2000-32319 A | 1/2000 |
| JP | 2000-49800 A | 2/2000 |
| JP | 2000-79587 A | 3/2000 |
| JP | 2000-196876 A | 7/2000 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-574 A | 1/2002 |
| JP | 2002-46088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-28066 A | 2/2005 |
| JP | 2005-59170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-7040 A | 1/2007 |
| JP | 2007-81646 A | 3/2007 |
| JP | 2007-232208 A | 9/2007 |
| JP | 2007-316966 A | 12/2007 |
| JP | 2009-125133 A | 6/2009 |
| JP | 2010-64154 A | 3/2010 |
| JP | 2010-532109 A | 9/2010 |
| JP | 2010-246954 A | 11/2010 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| WO | 93/06690 A1 | 4/1993 |
| WO | 97/42761 A1 | 11/1997 |
| WO | 98/51078 A1 | 11/1998 |
| WO | 99/67067 A1 | 12/1999 |
| WO | 00/25516 A1 | 5/2000 |
| WO | 00/33726 A1 | 6/2000 |
| WO | 01/31861 A1 | 5/2001 |
| WO | 03/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 3/2011 |
| WO | 2011/097130 A2 | 8/2011 |
| WO | 2011/097132 A2 | 8/2011 |
| WO | 2011/097132 A3 | 8/2011 |
| WO | 2011/109336 A2 | 9/2011 |
| WO | 2011/149902 A2 | 12/2011 |

OTHER PUBLICATIONS

"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.

Appeal from the U.S. District Court for the Central District of California in case No. 11-cv-9185, Judge Percy Anderson, Joint Appendix, vol. I of IV, Jun. 24, 2013, pp. A1-A6357.

Appeal from the U.S. District Court for the Central District of California in case No. 11-cv-9185, Judge Percy Anderson, Joint Appendix, vol. II of IV, Jun. 24, 2013, pp. A6849-A10634.

Appeal from the U.S. District Court for the Central District of California in case No. 11-cv-9185, Judge Percy Anderson, Joint Appendix, vol. III of IV, Jun. 24, 2013, pp. A10654-A15517.

Appeal from the U.S. District Court for the Central District of California in case No. 11-cv-9185, Judge Percy Anderson, Joint Appendix, vol. IV of IV, Jun. 24, 2013, pp. A15677-A18127.

Reply Brief for Defendant-Appellee VGO Communications, Inc., Appeal from the U.S. District Court for the Central District of California, in Case No. 2:11-cv-9185, Judge Percy Anderson, May 28, 2013, 75 pages.

Civil Minutes—General: Case No. Cv 11-9185PA (AJWx), *InTouch Tech., Inc.* v. *VGo Commons, Inc.*, U.S. District Court for the Central District of California, Judge Percy Anderson, Sep. 10, 2012, 7 pages.

Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 PA, May 14, 2012, 228 pages.

Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.

Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.

Active Media, Inc., "Saphira Software Manual", Real World, Saphira Version 5.3, 1997, 105 pages.

Apple Inc., "I Phone", iPhone Series, XP002696350, Sep. 21, 2012, pp. 1-29.

Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.

Bradner, S., "The Internet Standards Process—Revision 3", Network Working Group, Request for Comments: 2026, BCP: 9, Obsoletes: 1602, Category: Best Current Practice, Oct. 1996, pp. 1-36.

Christensen et al., "BeeSoft User's Guide and Reference", Robots for the Real World™, Real World Interface, Inc ., Sep. 26, 1997, 203 pages.

Chu et al., "Detection of Target Mobile Signal Strength", Technical Development, Motorola Inc., Jan. 1999, pp. 205-206.

Dario et al., "A Robot Workstation for Diagnosis and Physical Therapy", IEEE Catalog No. 88TH0234-5, Centro "E. Piaggio" University of Pisa, Italy, 1989, pp. 67-72.

Leifer et al., "VIPRR: A Virtually in Person Rehabilitation Robot", Proceedings of 1997 International Conference on Rehabilitation Robotics, Apr. 14-15, 1997, 4 pages.

Minsky, Marvin, "Telepresence", OMNI Magazine, Jun. 1980, 6 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

Reynolds et al., "Review of Robotic Telemedicine Utilization in Intensive Care Units (ICUs)", 11th Annual ATA Symposium, Tampa, Florida, 2011, 1 page.

(56) References Cited

OTHER PUBLICATIONS

Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, 7 pages.

UMASS Lowell Robotics Lab, "Robotics Lab @ UMASS Lowell", Department of Computer Science, Brochure, 2011, 2 pages.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon Creative Technology Transfer, A Global Affair, Apr. 1994, pp. 4-6.

Paulos et al., "A World Wide Web Telerobotic Remote Environment Browser", available online at <http://www.w3.org/Conferences/WWW4/Papers/326/>, retrieved on Nov. 23, 2010, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos et al., "PRoP: Personal Roving Presence", ACM:CHI Proceedings of CHI, 1998, 8 pages.

Paulos et al., "Ubiquitous Tele-Embodiment: Applications and Implications", International Journal of Human Computer Studies, vol. 46, No. 6, Jun. 1997, pp. 861-877.

Paulos et al., "Video of PRoP 2 at Richmond Field Station", www.prop.org, Printout of Home Page of Website and Two-page Transcript of the Audio Portion of said PRoP Video, May 2001, 2 pages.

Paulos, Eric J., "Personal Tele-Embodiment", Dissertation, Doctor of Philosophy in Computer Science in the Graduate Division of the University of California at Berkeley, 2001, 282 pages.

PictureTel Corporation, "Introducing PictureTel Live200 for Windows NT", 1997, 63 pages.

Pin et al., "A New Family of Omnidirectional and Holonomic Wheeled Platforms for Mobile Robots", IEEE Transactions on Robotics and Automation, vol. 10, No. 4, Aug. 1994, pp. 480-489.

Piquepaille, Roland, "How New Technologies are Modifying Our Way of Life", Roland Piquepaille's Technology Trends, This Blog and its RSS Feed Are Moving, Oct. 31, 2004, 2 pages.

Radvision, "Making Sense of Bandwidth the NetSense Way", Network Congestion in Unmanaged Networks Bandwidth Estimation and Adaptation Techniques, Radvision's Netsense Technology, 2010, 7 pages.

Roach, Adam, "Automatic Call Back Service in SIP", Internet Engineering Task Force, Internet Draft, Category: Informational, Mar. 2000, 8 pages.

Rovetta et al., "A New Telerobotic Application: Remote Laparoscopic Surgery Using Satellites and Optical Fiber Networks for Data Exchange", International Journal of Robotics Research, vol. 15, No. 3, Jun. 1, 1996, pp. 267-279.

Roy et al., "Towards Personal Service Robots for the Elderly", Workshop on Interactive Robots and Entertainment (WIRE 2000), vol. 25, Apr. 30-May 1, 2000, 7 pages.

Salemi et al., "MILO: Personal Robot Platform", IEEE/RSJ International Conference on Intelligent Robots and Systems, Aug. 2005, pp. 4089-4094.

Sandt et al., "Perception for a Transport Robot in Public Environments", Proceedings of the IEEE/RSJ International Conference on Intelligent Robots and Systems, vol. 1, Sep. 7-11, 1997, pp. 360-365.

Sawyer, Robert J., "Inventing the Future: 2000 Years of Discovery", Available online at <http://www.sfwriter.com/pritf.htm>, retrived on May 25, 2008, Jan. 2, 2000, 2 pages.

Schaeffer et al., "Care-O-Bot™: The Concept of a System for Assisting Elderly or Disabled Persons in Home Environments", Proceedings of the 24th Annual Conference of the IEEE Industrial Electronics Society, vol. 4, 1998, pp. 2476-2481.

Schultz et al., "Web Interfaces for Mobile Robots in Public Places", IEEE Robotics and Automation Magazine, vol. 7, No. 1, Mar. 2000, pp. 48-56.

Shimoga et al., "Touch and Force Reflection for Telepresence Surgery", Proceedings of the 16th Annual International Conference of the IEEE Engineering in Medicine and Biology Society, Nov. 1994, pp. 1049-1050.

Siegwart et al., "Interacting Mobile Robots on the Web", Proceedings of the IEEE International Conference on Robotics and Automation, May 1999, 7 pages.

Simmons et al., "Xavier: An Autonomous Mobile Robot on the Web", IEEE Robotics and Automation Magazine, 1999, pp. 43-48.

Stephenson, Gary, "Dr. Robot Tested at Hopkins", Johns Hopkins Medical institutions, available online at <http://www.hopkinsmedicine.org/press/2003/august/030805.htm>, Aug. 5, 2003, 2 pages.

Stoianovici et al., "Robotic Tools for Minimally Invasive Urologic Surgery", Complications of Urologic Laparoscopic Surgery: Recognition, Management and Prevention, Dec. 2002, 17 pages.

Suplee, Carl, "Mastering the Robot", available online at <http://www.cs.cmu.edu-nursebotlweb/press/wash/index.html>, retrieved on Nov. 23, 2010, Sep. 17, 2000, 5 pages.

Tahboub et al., "Dynamics Analysis and Control of a Holonomic Vehicle With a Continuously Variable Transmission", Journal of Dynamic Systems, Measurement and Control ASME, vol. 124, Mar. 2002, pp. 118-126.

Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.

Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.

Theodosiou et al., "MuLVAT: A Video Annotation Tool Based on XML-Dictionaries and Shot Clustering", 19th International Conference, Artificial Neural Networks—ICANN, Sep. 14-17, 2009, pp. 913-922.

Thrun et al., "Probabilistic Algorithms and the Interactive Museum Tour-Guide Robot Minerva", Journal of Robotics Research, vol. 19, 2000, pp. 1-35.

Time, Lists, "Office Coworker Robot", Best Inventions of 2001, Available online at <http://content.time.com/time/specials/packages/article/0,28804,1936165_1936255_1936640,00.html>, Nov. 19, 2001, 2 pages.

Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.

Tzafestas et al., "VR-based Teleoperation of a Mobile Robotic Assistant: Progress Report", Technical Report DEMO 2000/13, Institute of Informatics and Telecommunications, National Center for Scientific Research "Demokritos", Athens, Greece, Nov. 2000, pp. 1-23.

Urquhart, Kim, "InTouch's Robotic Companion 'Beams Up' Healthcare Experts", Medical Device Daily, The Daily Medical Technology Newspaper, vol. 7, No. 39, Feb. 27, 2003, 2 pages.

Weaver et al., "Monitoring and Controling Using the Internet and Java", Proceedings of the 25th Annual Conference of the IEEE Industrial Electronics Society, vol. 3, 1999, pp. 1152-1158.

Weiss et al., "Telework and Video-Mediated Communication: Importance of Real-Time, Interactive Communication for Workers with Disabilities", Available online at <http://www.telbotics.com/research_3.htm>, retrieved on Nov. 23, 2010, 1999, 3 pages.

Weiss, et al., "PEBBLES: A Personal Technology for Meeting Education, Social and Emotional Needs of Hospitalised Children", Personal and Ubiquitous Computing, vol. 5, No. 3, Aug. 2001, pp. 157-168.

West et al., "Design of Ball Wheel Mechanisms for Omnidirectional Vehicles with Full Mobility and Invariant Kinematics", Journal of Mechanical Design, ASME, vol. 119, Jun. 1997, pp. 153-161.

Yamasaki et al., "Applying Personal Robots and Active Interface to Video Conference Systems", 6th International Conference on Human Computer Interaction, vol. B, 1995, pp. 243-248.

Yamauchi, Brian, "PackBot: A Versatile Platform for Military Robotics", Proceedings of SPIE for Military Robotics, 2004, pp. 228-237.

(56) References Cited

OTHER PUBLICATIONS

Yong et al., "Robot Task Execution with Telepresence Using Virtual Reality Technology", International Conference on Mechatronic Technology, Nov. 30-Dec. 2, 1998, pp. 1-8.

Zambroski, James, "CMU, Pitt Developing 'Nursebot'", available online at <http://www.cs.cmu.edu/~nursebot/web/press/tribunereview.html>, retrieved on Jun. 26, 2012, Oct. 27, 2000, 3 pages.

Zamrazil, Kristie, "Telemedicine in Texas: Public Policy Concerns", Focus Report, House Research Organization, Texas House of Representatives, No. 76-22, May 5, 2000, pp. 1-16.

Zipperer, Lorri, "Robotic Dispensing System", ISMP Medication Safety Alert, vol. 4, No. 17, Aug. 25, 1999, pp. 1-2.

Zorn, Benjamin G., "Ubiquitous Telepresence", Department of Computer Science, University of Colorado, Mar. 18, 1996, 13 pages.

"Defendant VGo Communications, Inc.'s Invalidity Contentions Pursuant to the Feb. 27, 2012 Civil Minute Order", U.S. District Court for the Central District of California, in Case No. CV11-9185 PA, May 2, 2012, 143 pages.

"Magne Charge", Smart Power for Electric Vehicles, General Motors Corporation, Serial No. 75189637, Registration No. 2114006, Filing Date: Oct. 29, 1996, Aug. 26, 1997, 2 pages.

"More Online Robots: Robots that Manipulate", available online at <http://ford.ieor.berkeley.edu/ir/robots_a2.html>, retrieved on Nov. 23, 2010, Aug. 2001, 2 pages.

"PictureTel Adds New Features and Functionality to its Award-Winning Live200 Desktop Videoconferencing System", PR Newswire Association, LLC Gale, Cengage Learning, Jun. 13, 1997, 4 pages.

"Appeal from the U.S. District Court for the Central District of California in No. 11-CV-9185, Judge Percy Anderson", May 9, 2014, pp. 1-48.

"Google Translation of: Innovations Report", From Research Project to Television Star: Care-O-bot in ZDF Series, available at <http://www.innovations-report.de/specials/printa.php?id=5157>, Sep. 28, 2001, 2 pages.

"MPEG File Format Summary", available at <http://www.fileformat.info/format/mpeg/egff.htm>, retrieved on Jun. 25, 2014, Feb. 1, 2001, 7 pages.

Koenen, Rob, "MPEG-4: A Powerful Standard for Use in Web and Television Environments", (KPN Research), available at <http://www.w3.org/Architecture/1998/06/Workshop/paper26>, Jul. 1, 1998, 4 pages.

Nomadic Technologies, Inc., "Nomad Scout User's Manual", Software Version 2.7, Part No. DOC00004, Jul. 12, 1999, pp. 1-59.

ACM Digital Library Record, Autonomous Robots, vol. 11, No. 1, Table of Content, available at <http://dl.acm.org/citation.cfm?id=591550&picked=prox&cfid=360891374&cftoken=35225929>, Jul. 2001, 2 pages.

Brenner, Pablo, "A Technical Tutorial on the IEEE 802.11 Protocol", BreezeCOM Wireless Communications, Jul. 18, 1996, pp. 1-24.

CMU Course, "16×62 Robot User's Manual", (Describing the Nomad Scout), Carnegie Mellon University, Feb. 1, 2001, 11 pages.

Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.

Panusopone et al., "Performance Comparison of MPEG-4 and H.263+ for Streaming Video Applications", Circuits Systems Signal Processing, vol. 20, No. 3, 2001, pp. 293-309.

Paulos et al., "Personal Tele-Embodiment", Chapter 9 in Goldberg et al., Ed., "Beyond Webcams", MIT Press, Jan. 4, 2002, pp. 155-167.

Paulos et al., "Social Tele-Embodiment: Understanding Presence", Autonomous Robots, vol. 11, No. 1, Kluwer Academic Publishers, Jul. 2001, pp. 87-95.

Paulos, Eric John, "Personal Tele-Embodiment", Introductory and Cover pp. from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).

Paulos, Eric John, "Personal Tele-Embodiment", OskiCat Catalog Record, UCB Library Catalog, Results page and MARC Display, retrieved on Jun. 14, 2014, 3 Pages.

Schraft et al., "Care-O-bot™: The Concept of a System for Assisting Elderly or Disabled Persons in Home Enviornments", IEEE Proceedings of the 24th Annual Conference of the Industrial Electronics Society, IECON '98, Aug. 31-Sep. 4, 1998, pp. 2476-2481.

Harmo et al., "Moving Eye—Interactive Telepresence over Internet with a Ball Shaped Mobile Robot", Automation Technology Laboratory, Helsinki University of Technology, 2000, 6 pages.

Haule et al., "Control Scheme for Delayed Teleoperation Tasks", Communications, Computers and Signal Processing, Proceedings of IEEE Pacific Rim Conference, May 17-19, 1995, pp. 157-160.

Hees, William P., "Communications Design for a Remote Presence Robot", CSCI E-131B, Final Project, Jan. 14, 2002, 12 pages.

Herias et al., "Flexible Virtual and Remote Laboratory for Teaching Robotics", FORMATEX 2006, Proceedings of Advance in Control Education Madrid, Spain, Jun. 2006, pp. 1959-1963.

Holmberg et al., "Development of a Holonomic Mobile Robot for Mobile Manipulation Tasks", FSR'99 International Conference on Field and Service Robotics, Pittsburgh, PA, Aug. 1999, 6 pages.

Ishiguro et al., "Integrating a Perceptual Information Infrastructure with Robotic Avatars: A Framework for Tele-Existence", Intelligent Robots and Systems, Proceedings of 1999 IEEE/RSJ International Conference, vol. 2, 1999, pp. 1032-1038.

Ishihara et al., "Intelligent Microrobot DDS (Drug Delivery System) Measured and Controlled by Ultrasonics", Proceedings of IEEE/RSJ International Workshop on Intelligent Robots and Systems, vol. 2, Nov. 3-5, 1991, pp. 1145-1150.

ITU, "Call Completion Supplementary Services for H.323", ITU-T, Telecommunication Standardization Sector of ITU, H.450.9, Series H: Audiovisual and Multimedia Systems, Nov. 2000, 63 pages.

ITU, "Call Intrusion Supplementary Service for H.323", ITU-T, Telecommunication Standardization Sector of ITU, H.450.11, Series H: Audiovisual and Multimedia Systems, Mar. 2001, 59 pages.

ITU, "Packet-Based Multimedia Communications Systems", ITU-T, Telecommunication Standardization Sector of ITU, H.323, Series H: Audiovisual and Multimedia Systems, Feb. 1998, 128 pages.

ITU, "A Far End Camera Control Protocol for Videoconferences Using H.224", Transmission of Non-Telephone Signals, ITU-T, Telecommunication Standardization Sector of ITU, H.281, Nov. 1994, 12 pages.

Ivanova, Natali, "Internet Based Interface for Control of a Mobile Robot", First Degree Programme in Mathematics and Computer Science, Masters thesis, Department of Numerical Analysis and Computer Science, 2003, 59 pages.

Jacobs et al., "Applying Telemedicine to Outpatient Physical Therapy", AMIA, Annual Symposium Proceedings, 2002, 1 page.

Jenkins et al., "Telehealth Advancing Nursing Practice", Nursing Outlook, vol. 49, No. 2, Mar. 2001, pp. 100-105.

Johanson, Mathias, "Supporting Video-Mediated Communication over the Internet", Thesis for the degree of Doctor of Philosophy, Department of Computer Engineering, Chalmers University of Technology, Gothenburg, Sweden, 2003, 222 pages.

Jouppi et al., "BiReality: Mutually-Immersive Telepresence", Multimedia '04, Proceedings of the 12th Annual ACM International Conference on Multimedia, Oct. 10-16, 2004, pp. 860-867.

Jouppi et al., "First Steps Towards Mutually-Immersive Mobile Telepresence", CSCW '02, Proceedings of the ACM conference on Computer Supported Cooperative Work, Nov. 16-20, 2002, pp. 354-363.

Kanehiro et al., "Virtual Humanoid Robot Platform to Develop Controllers of Real Humanoid Robots without Porting", Proceedings of IEEE/RSJ International Conference on Intelligent Robots and Systems, vol. 2, Oct. 29-Nov. 3, 2001, pp. 1093-1099.

Kaplan et al., "An Internet Accessible Telepresence", Multimedia Systems Journal, vol. 5, 1996, 7 pages.

Keller et al., "An Interface for Raven", The National Aviary's Teleconferencing Robot, Interaction and Visual Interface Design, School of Design, Carnegie Mellon University, 2001, 8 pages.

Khatib et al., "Robots in Human Environments", Robotics Laboratory, Department of Computer Science, Stanford University, 1999, 15 pages.

(56) References Cited

OTHER PUBLICATIONS

Knight et al., "Active Visual Alignment of a Mobile Stereo Camera Platform", Robotics and Automation, Proceedings of ICRA '00, IEEE International Conference, vol. 4, Apr. 24-28, 2000, pp. 3203-3208.

Kurlowicz et al., "The Mini Mental State Examination (MMSE)", The Hartford Institute for Geriatric Nursing, Journal of Psychiatric Research, No. 3, Jan. 1999, 2 pages.

Kuzuoka et al., "Can the GestureCam be a Surrogate?", Proceedings of the Fourth European Conference on Computer-Supported Cooperative Work, Sep. 10-14, 1995, pp. 181-196.

Lane, Earl, "Automated Aides", available online at <http://www.cs.cum.edu/nursebot/web/press/nd4380.htm>, Reterieved on Nov. 23, 2010, Oct. 17, 2000, 4 pages.

Lee et al., "A Novel Method of Surgical Instruction: International Telementoring", World Journal of Urology, vol. 16, No. 6, Dec. 1998, pp. 367-370.

Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.

Lim et al., "Control to Realize Human-Like Walking of a Biped Humanoid Robot", Systems, Man and Cybernetics, IEEE International Conference, vol. 5, 2000, pp. 3271-3276.

Linebarger et al., "Concurrency Control Mechanisms for Closely Coupled Collaboration in Multithreaded Virtual Environments", Department of Computer Science and Engineering; Lehigh University, vol. 13, 2004, 40 pages.

Sachs et al., "Virtual Visit™: Improving Communication for Those Who Need it Most", Studies in Health Technology and Informatics, vol. 94, Medicine Meets Virtual Reality 11, 2003, pp. 302-308.

Long, William F., "Robot Navigation Technology", available online at <http://www.atp.nist.gov/eao/sp950-1/helpmate.htm>, retrieved on Nov. 23, 2010, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, Feb. 7, 2001, pp. 568-572.

Mair, G. M., "Telepresence—The Technology and its Economic and Social Implications", Technology and Society, Technology and Society at a Time of Sweeping Change, Proceedings of International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilising New Technology in Design Education", Loughborough University, IDater, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", available online at <http://www.pcmag.com/article2/0,2817,1130820,00.asp>, Jul. 1, 2003, 4 pages.

Michaud, Anne, "Introducing 'Nursebot'", available online at <http://www.cs.cmu.edu/~nursebot/web/press/globe_3_01/index.html>, retrieved on May 5, 2008, Sep. 11, 2001, 4 pages.

Microsoft Corporation, Inc., "Microsoft NetMeeting 3 Features", available online at <http://technet.microsoft.com/en-us/library/cc723477.aspx>, retrieved on Jun. 26, 2012, 6 pages.

Montemerlo, Mike, "Telepresence: Experiments in Next Generation Internet", available Online at <http://www.ri.cmu.edu/creative/archives.htm>, retrieved on May 25, 2008, Oct. 20, 1998, 3 pages.

Murphy, Robin R., "Introduction to AI Robotics", A Bradford Book, The Massachusetts Institute of Technology Press, 2000, 487 pages.

Nakajima et al., "A Multimedia Teleteaching System using an Electronic Whiteboard for Two-Way Communication of Motion Videos and Chalkboards", Robot and Human Communication, Proceedings of 2nd IEEE International Workshop, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "Group-Oriented User Interface for Digital Image Management", Journal of Visual Languages and Computing, vol. 14, No. 4, Aug. 2003, pp. 45-46.

Nersc, "Berkeley Lab's Rage Telepresence Robot Captures R&D100 Award", Available online at <https://www.nersc.gov/news-publications/news/nersc-center-news/2002/berkeley-lab-s-rage-telepresence-robot-captures-r-and-d100-award/>, Retrieved on Jan. 22, 2014, Jul. 2, 2002, 2 pages.

"Nomad XR4000 Hardware Manual", Release 1.0, Nomadic Technologies, Inc., Mar. 1999, 34 pages.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental evaluation of the Emotional Communication between Robots and Humans", Proceedings of the 2000 IEEE/RSJ International Conference on Intelligent Robots and Systems, vol. 1, 2000, pp. 175-180.

Ogata et al., "Emotional Communication Robot: WAMOEBA-2R-Emotion Model and Evaluation Experiments", Proceedings of the International Conference on Humanoid Robots, 2000, pp. 1-16.

Office Action received for Chinese Patent Application No. 200680044698.0 on Nov. 4, 2010. (9 pages of Official Copy and 17 pages of English Translation).

Wang et al., "A Healthcare Tele-robotic System with a Master Remote Station with an Arbitrator", U.S. Appl. No. 60/449,762, filed Feb. 24, 2003, 28 pages.

Activmedia Robotics LLC, "Pioneer 2/PeopleBot™", Operations Manual, Version 9, Oct. 2001, 78 pages.

Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.

Ando et al., "A Multimedia Self-Service Terminal with Conferencing Functions", Proceedings of 4th IEEE International Workshop on Robot and Human Communication, RO-MAN'95, Jul. 5-7, 1995, pp. 357-362.

Android Amusement Corp., "Renting Robots from Android Amusement Corp!", What Marketing Secret, (Advertisement), 1982, 1 page.

Applebome, "Planning Domesticated Robots for Tomorrow's Household", New York Times, available online at <http://www.theoldrobots.com/images17/dc17.JPG>, Mar. 4, 1982, 1 page.

Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, 8 pages.

Barrett, Rick, "Video Conferencing Business Soars as Companies Cut Travel; Some Travel Cuts are Permanent", available online at <http://www.ivci.com/international_videoconferencing_news_videoconferencing_news_19.html>, May 13, 2002, 2 pages.

Bartholomew, "Pharmacy Apothecary of England", BnF-Teaching Kit—Childhood in the Middle Ages, available online at <http://classes.bnf.fr/ema/grands/034.htm>, retrieved on Jul. 26, 2012, 2 pages.

Bauer et al., "Remote Telesurgical Mentoring: Feasibility and Efficacy", IEEE, Proceedings of the 33rd Hawaii International Conference on System Sciences, 2000, pp. 1-9.

Bauer, Jeffrey C., "Service Robots in Health Care: The Evolution of Mechanical Solutions to Human Resource Problems", BonSecours Health System, Inc., Technology Ealy Warning System, Jun. 2003, pp. 1-10.

Bischoff, Rainer, "Design Concept and Realization of the Humanoid Service Robot HERMES", In A. Zelinsky (ed.): Field and Service Robotics, Springer, London, 1998, pp. 485-492.

Blackwell, Gerry, "Video: A Wireless LAN Killer App?", Availabel online at <http://www.wi-fiplanet.com/columns/article.php/1010261/Video-A-Wireless-LAN-Killer>, retrieved on Nov. 22, 2010, Apr. 16, 2002, 4 pages.

(56) References Cited

OTHER PUBLICATIONS

Breslow et al., "Effect of a Multiple-Site Intensive Care Unit Telemedicine Program on Clinical and Economic Outcomes: An Alternative Paradigm for Intensivist Staffing", Critical Care Med., vol. 32, No. 1, Jan. 2004, pp. 31-38.
Brooks, Rodney A., "A Robust Layered Control System for a Mobile Robot", IEEE, Journal of Robotics and Automation, vol. 2, No. 1, Mar. 1986, pp. 14-23.
Brooks, Rodney Allen, "Flesh and Machines: How Robots Will Change Us", available online at <http://dl.acm.org/citation.cfm?id=560264&preflayout=flat%25202%2520of>, retrieved on Nov. 23, 2010, Feb. 2002, 3 pages.
Celt et al., "The eICU: It's Not Just Telemedicine", Critical Care Medicine, vol. 29, No. 8 (Supplement), Aug. 2001, pp. 183-189.
Cheetham et al., "Interface Development for a Child's Video Conferencing Robot", Centre for Learning Technologies, Ryerson University, 2000, 4 pages.
Cleary et al., "State of the Art in Surgical Robotics: Clinical Applications and Technology Challenges", Computer Aided Surgery, Nov. 2001, pp. 1-26.
CNN, "Floating 'Droids' to Roam Space Corridors of the Future", available online at <http://edition.cnn.com/2000/TECH/space/01/12/psa/> retrieved on Nov. 11, 2010., Jan. 12, 2000, 3 pages.
CNN.com, "Paging Dr. Robot: Machine Helps Doctors with Patients", available online at <http://edition.cnn.com/2003/TECH/ptech/09/29/doctor.robot.ap/index.html>, retrieved on Sep. 30, 2003, 3 pages.
Crowley, Susan L., "Hello to Our Future", AARP Bulletin, available online at <http://www.cs.cmu.ed/-nursebot/web/press/aarp 99_14/millennium.html>, Jan. 2000, retrieved on Nov. 23, 2010, 12 pages.
Dalton, Barnaby, "Techniques for Web Telerobotics", Ph. D Thesis for degree of Doctor of Philosophy, University of Western Australia, available online at <http://telerobot.mech.uwa.edu.au/information.html>, 2001, 243 pages.
Davies, Brian, "Robotics in Minimally Invasive Surgery", Mechatronics in Medicine Lab, Dept. Mechanical Engineering, Imperial College, London SW7 2BX, The Institution of Electrical Engineers, IEE, Savoy Place, London WC2R OBL, UK, 1995, pp. 1-2.
Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic_set=>, retrieved on Jul. 7, 2012, Sep. 2000, 3 pages.
Dean et al., "1992 AAAI Robot Exhibition and Competition", Articles, AI Magazine, vol. 14, No. 1, 1993, 15 pages.
Digiorgio, James, "Is Your Emergency Department of the Leading Edge?", Chicago Hospital News, vol. 2, No. 12, Feb. 2005, 3 pages.
Dudenhoeffer et al., "Command and Control Architectures for Autonomous Micro-Robotic Forces", FY00 Project Report, Idaho National Engineering and Environmental Laboratory, Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, Jun. 2000, 10 pages.
Elhajj et al., "Supermedia in Internet-Based Telerobotic Operations", Lecture Notes in Computer Science, vol. 2216, 2001, pp. 359-372.
Elhajj et al., "Synchronization and Control of Supermedia Transmission via the Internet", Proceedings of 2001 International Symposium on Intelligent Multimedia Video and Speech Processing, Hong Kong, May 2-4, 2001, pp. 320-323.
Ellison et al., "Telerounding and Patient Satisfaction after Surgery", American College of Surgeons, Elsevier, Inc., vol. 199, No. 4, Oct. 2004, pp. 523-530.
Fels et al., "Developing a Video-Mediated Communication System for Hospitalized Children", Telemedicine Journal, vol. 5, No. 2, 1999, 30 pages.
Fetterman, David M., "Videoconferencing Over the Internet", Qualitative Health Journal, vol. 7, No. 1, May 1966. pp. 154-163.
Fiorini et al., "Health Care Robotics: A Progress Report", IEEE International Conference on Robotics and Automation, vol. 2, Apr. 20-25, 1997, pp. 1271-1276.
Fong, Terrence, "Collaborative Control: A Robot-Centric Model for Vehicle Teleoperation", The Robotics Institute Carnegie Mellon University, Nov. 2001, 197 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, San Francisco, California, 2000, pp. 2019-2024.
Goldberg et al., "Desktop Teleoperation via the World Wide Web", Proceedings of IEEE International Conference on Robotics and Automation, vol. 1, May 21-27, 1995, pp. 654-659.
Goldenberg et al., "Telemedicine in Otolaryngology", American Journal of Otolaryngology, vol. 23, No. 1, Jan. 2002, pp. 35-43.
Goldman, Lea, "Machine Dreams", available online at <http://www.forbes.com/global/2002/0527/043.html>, retrieved on Nov. 23, 2010., May 27, 2002, 5 pages.
Gump, Michael D., "Robot Technology Improves VA Pharmacies", U.S. Medicine Informational Central, Jul. 2001, 3 pages.
Hameed et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, Kluwer Acedemic Publishers, vol. 29, Nov. 2000, pp. 257-275.
Handley et al., "SDP: Session Description Protocol", RFC 2327, available Online at <http://www.faqs.org/rfcs/rfc2327.html>, retrieved on Nov. 23, 2010, Apr. 1998, 22 pages.
Hanebeck et al., "ROMAN: A Mobile Robotic Assistant for Indoor Service Applications", Proceedings of the IEEE/RSJ International Conference on Intelligent Robots and Systems, vol. 2, 1997, pp. 518-525.

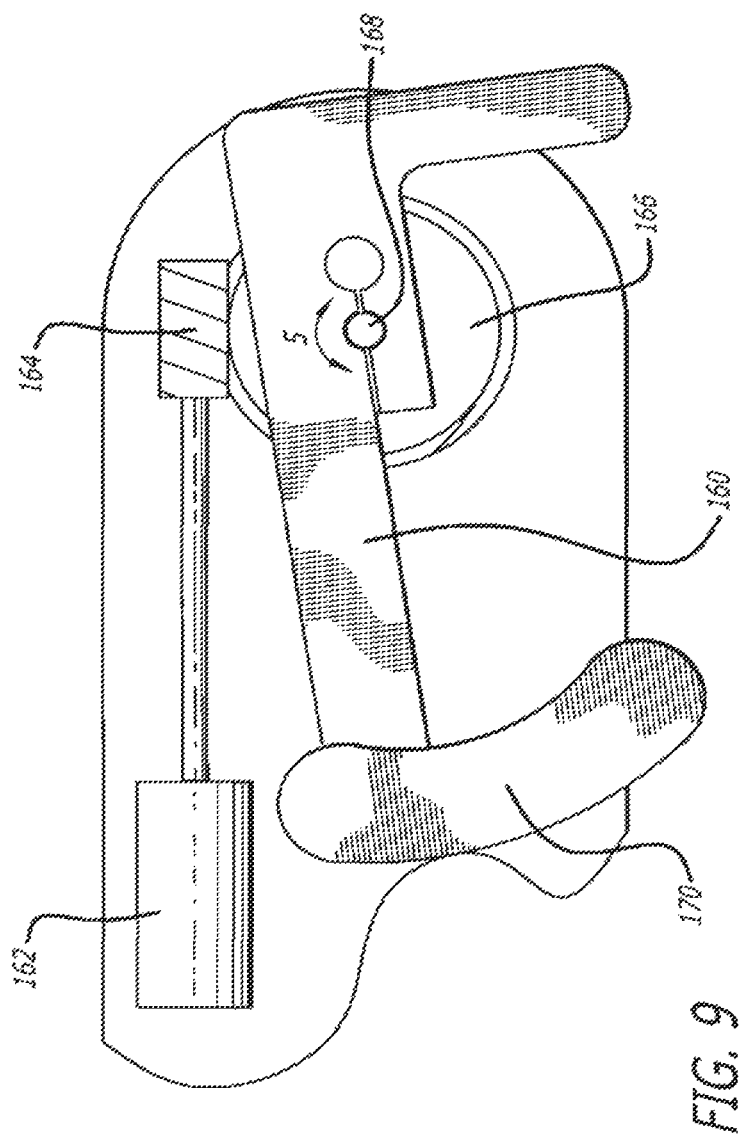

MOBILE ROBOT WITH A HEAD-BASED MOVEMENT MAPPING SCHEME

CROSS REFERENCE TO RELATED APPLICATIONS

This application is a continuation of application Ser. No. 12/413,038, filed Mar. 27, 2009, pending, which is a divisional of application Ser. No. 10/890,891, filed Jul. 13, 2004, now U.S. Pat. No. 8,077,963.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel.

The assignee of this invention(s), InTouch-Health, Inc. markets a remote controlled mobile robot under the trademark COMPANION that can be used by medical personnel to remotely "visit" patients. The COMPANION system includes a mobile robot with a camera, monitor, microphone, speakers, and other equipment that allow for two-way audio/visual communication between the patient and someone operating the system from a remotely located computer.

The COMPANION system includes a joystick that can be manipulated to move a mobile platform of the robot. A forward pivot of the joystick causes a corresponding forward movement of the mobile platform. The joystick button can be depressed to move the camera and allow the user to pan a room. Unfortunately, panning the camera may cause the forward viewing direction depicted by the screen to be different than the forward vector of the mobile platform. A forward pivot of the joystick will cause an angular movement of the robot relative to the field of view provided by the robot camera. This can cause disorientation and in general complicates movement of the robot.

BRIEF SUMMARY OF THE INVENTION

A mobile robot system that is controlled through an input device. The system includes a robot that has a camera located in a camera reference coordinate system, and a mobile platform. The input device causes movement of the camera, and movement of the mobile platform within the camera reference coordinate system.

BRIEF DESCRIPTION OF THE DRAWINGS

FIG. 9 is a sectional view showing an actuator of the pedestal assembly.

DETAILED DESCRIPTION

Disclosed is a robotic system that includes a mobile robot and a remote input device. The input device may be a joystick that is used to move a camera and a mobile platform of the robot. The system may operate in a mode where the mobile platform moves in a camera reference coordinate system. The camera reference coordinate system is fixed to a viewing image provided by the camera so that movement of the robot corresponds to a direction viewed on a screen. This prevents disorientation during movement of the robot if the camera is panned across a viewing area.

Figure 1:
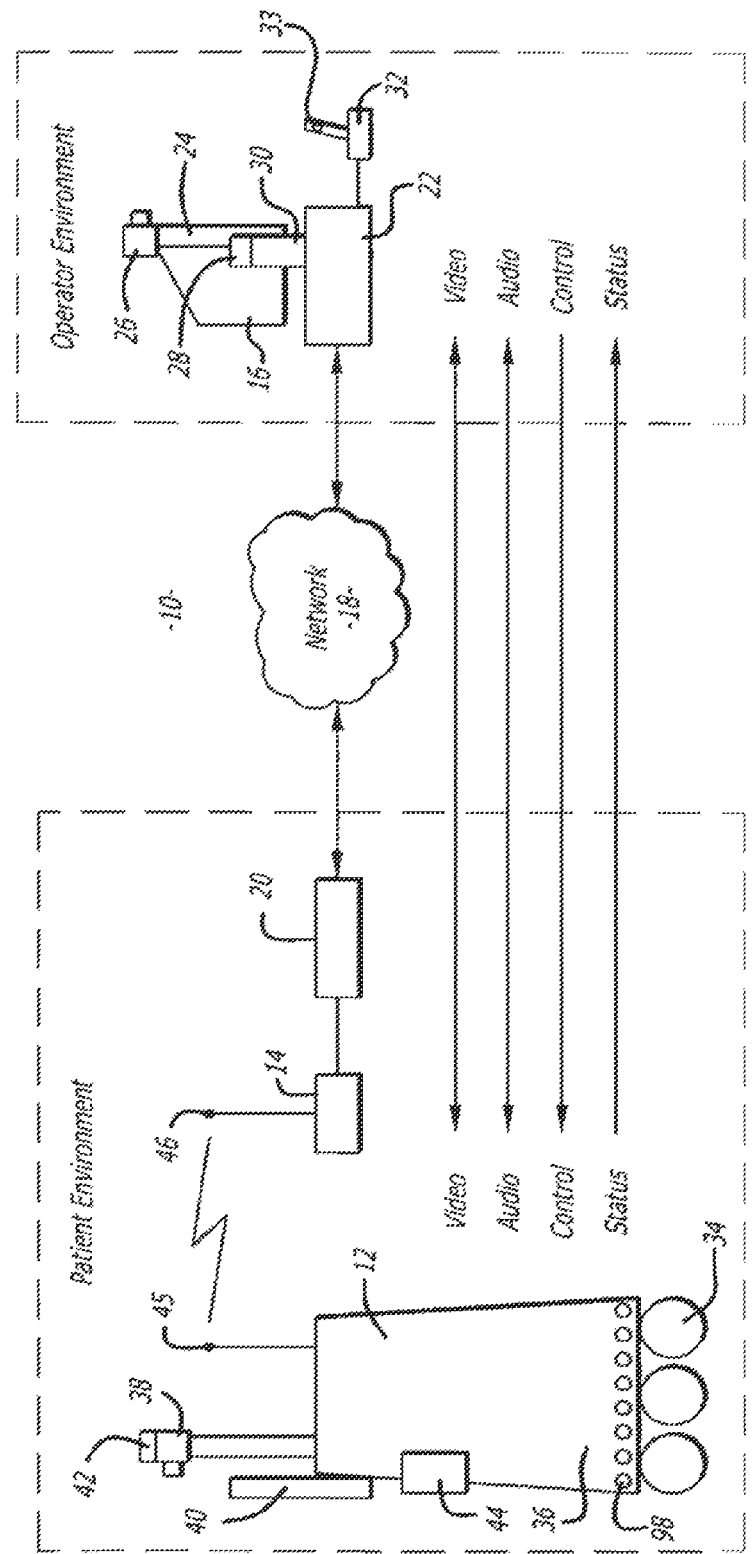
FIGS. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN), or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The joystick 32 may have a toggle button 33 that allows the system to operate in two different modes. In one mode the robot moves in a platform reference coordinate system. In another mode the robot moves in a camera reference coordinate system.

The control station 16 is typically located in a place that is remote from the robot 12. Although only one robot 12 and one station 16 are shown, it is to be understood that the system 10 may have a plurality of robots 12 and/or a plurality of remote stations that communicate through the broadband network. In general any number of robots 12 may be controlled by any number of remote stations 16. For example, one remote station 16 may be coupled to a plurality of robots 12, or one robot 12 may be coupled to a plurality of remote stations 16.

The robot 12 includes a mobile platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
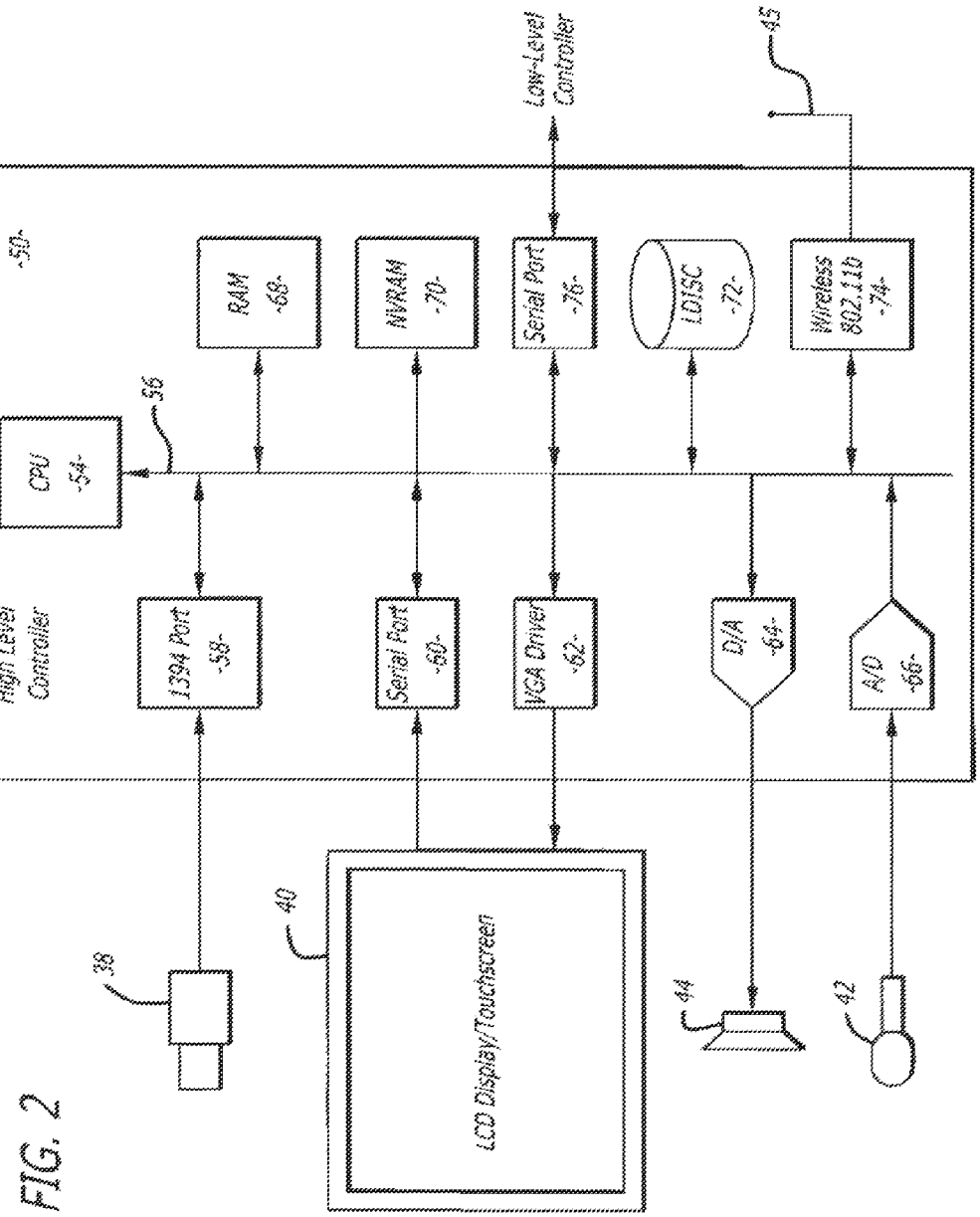
FIG. 2 is a schematic of an electrical system of a robot.
Figure 3:
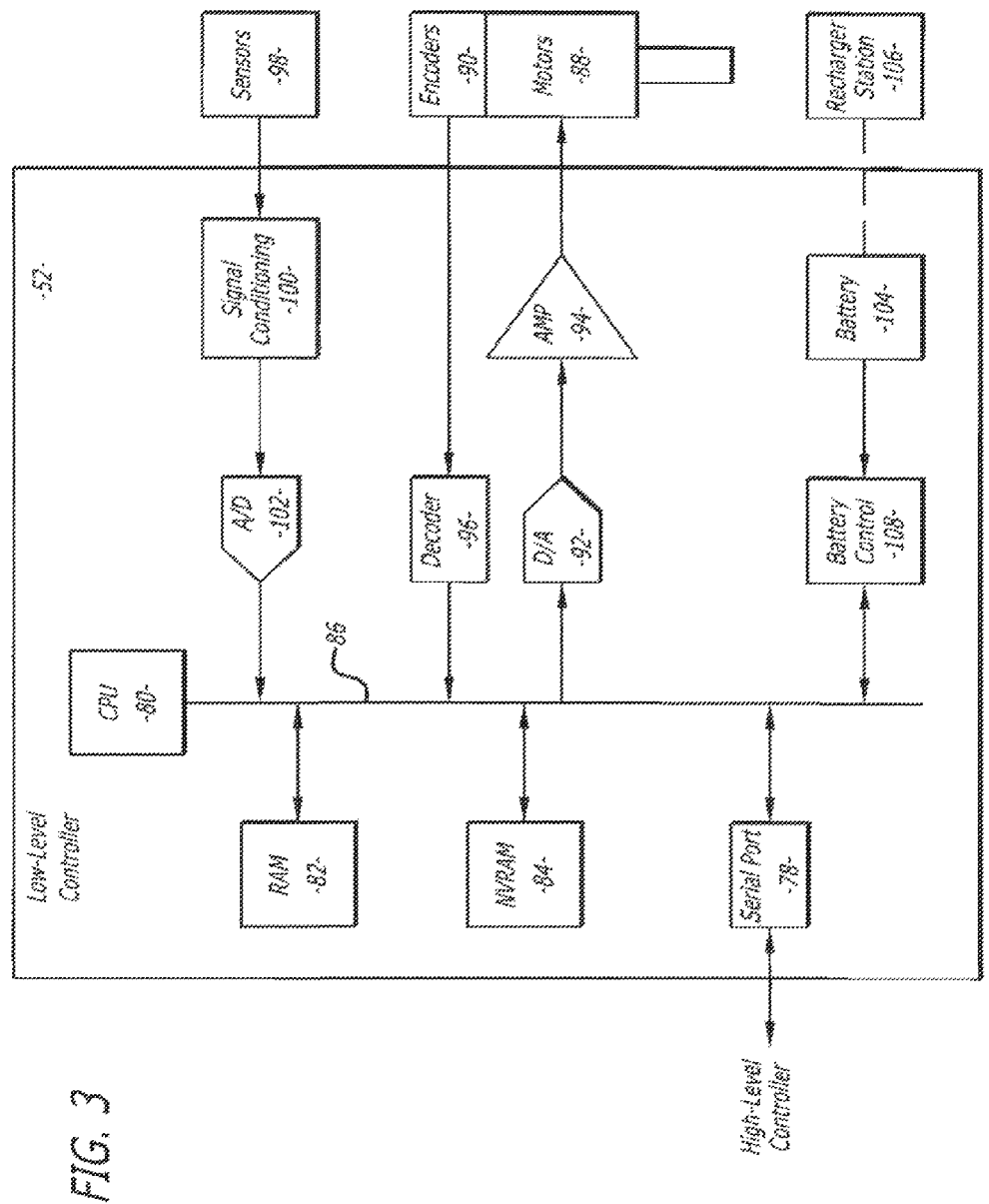
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station 16. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
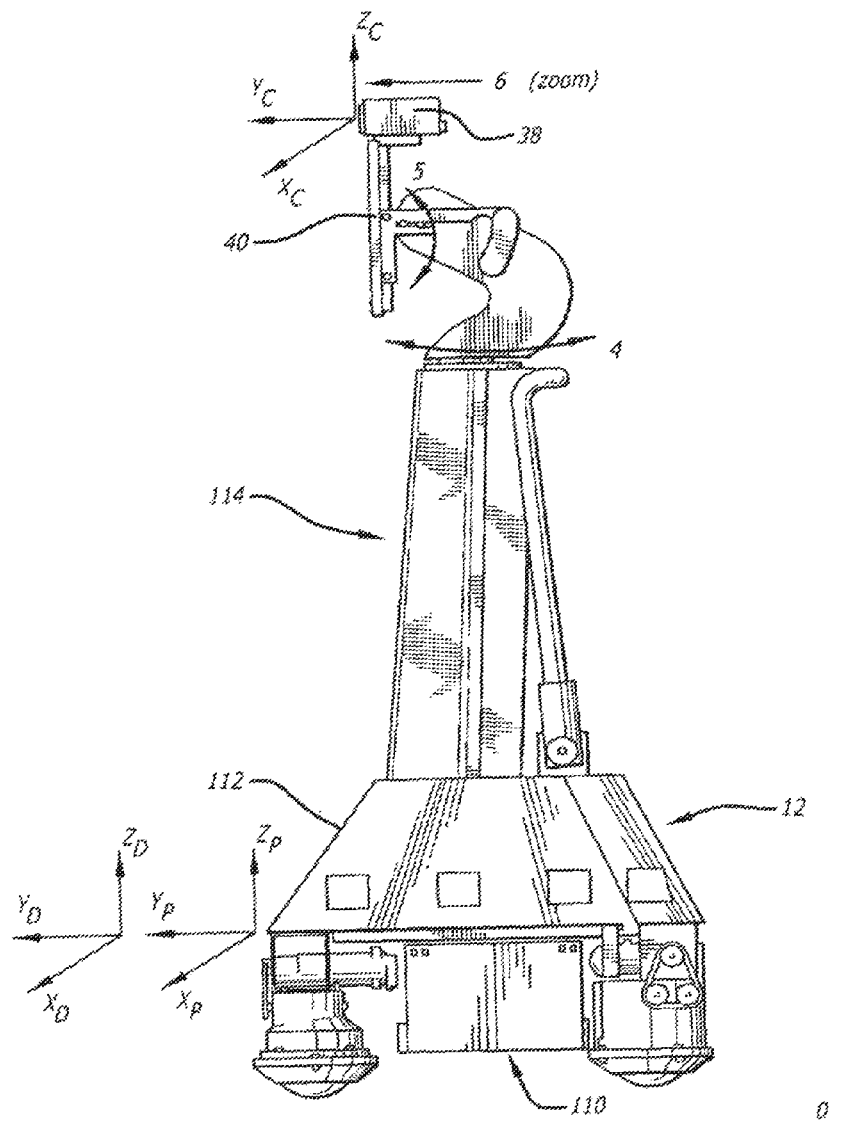
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have a pedestal assembly 114 that supports the camera 38 and the monitor 40. The pedestal assembly 114 may have two degrees of freedom so that the camera 26 and monitor 24 can be swiveled and pivoted as indicated by the arrows.

The platform 110 is located within a platform reference coordinate system that may have axes Xp, Yp and Zp. By way of example, the y-axis Yp may extend from a nose of the platform 110. The camera 38 is fixed to a camera reference coordinate system that may have axes Xc, Yc and Zc. The y-axis Yc may extend perpendicular from the camera lens. When the robot is initialized, the y-axis Yc of the camera coordinate system may be aligned with the y-axis Yp of the platform coordinate system. A forward pivoting of the joystick 32 (shown in FIG. 1) may cause a corresponding movement of the platform 110 in the direction of the y-axis Yp in the platform coordinate system.

The robot may have a drive vector that may have axes Xd, Yd, and Zd that is mapped to the camera coordinate system, the platform coordinate system or some other system. By way of example, the y-axis Yp may extend in the direction of forward motion. Mapping includes the process of transforming an input command into a directional movement relative to one or more coordinate systems. The robot controller may perform certain algorithms to translate input commands to platform movement in accordance with a specified mapping scheme. For example, when the drive vector is mapped to the camera coordinate system the controller computes the drive vector of the input command relative to the camera coordinate system. In a platform mapping scheme the input drive vector is computed relative to the platform coordinate system. In yet another scheme the drive vector can be computed relative to another coordinate system, such as a world coordinate system (eg. coordinate system relative to the ground) that is independent of the camera or platform coordinate systems. Mapping the drive vector to the camera coordinate system may be desirable because all movement would be relative to the image viewed by the user, providing a system that is intuitive to use.

A twisting of the joystick 32 may cause the camera 38 to swivel as indicated by arrows 4. For example, if the joystick 32 is twisted +45 degrees the camera 38 will pivot +45 degrees. Swiveling the camera 38 also moves the y-axis Yc of the camera coordinate system, because the y-axis Yc is fixed to the camera. This may be different than the drive direction. The remote station computer may operate a program to generate a command that will automatically rotate the platform 110 to realign the y-axis Yp of the platform coordinate system with the y-axis Yc of the camera coordinate system. For the above example, the platform 110 is rotated +45 degrees. This approach keeps the platform 110 aligned with the camera 38, so that any subsequent movement of the robot will be intuitive relative to the image provided by the camera. For example, a forward pivot of the joystick will induce a forward movement of the robot as viewed through the monitor of the remote station. In this driving scheme, the platform may not be aligned with the head. The computer may generate trajectory planning for the platform coordinate system to move into alignment with the head coordinate system over a period of time or distance traveled, with or without an initial delay in time or some distance.

Figure 5:
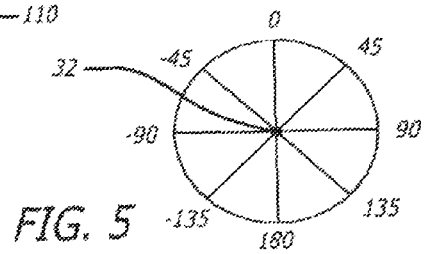
FIG. 5 is an illustration of a mapping scheme for a joystick of the system.

The system may be configured so that pivotal movement of the joystick 32 may be mapped to a corresponding directional movement of the robot as shown in FIG. 5. For example, pivoting the joystick along the +45 degree line shown in FIG. 5 may cause the robot to move in a +45 degree direction relative to the y-axis Yc of the camera coordinate frame. Alternatively, the camera may pan +45 degrees and the platform 110 may rotate +45 degrees before forward movement by the robot. The automatic panning and platform rotation causes the robot to move in a forward direction as depicted by the image provided by the camera. The robot may have a mode wherein the user can twist the joystick to pan the camera during robot movement such that the movement is not in the direction the camera is pointing. This allows the user to visually pan while moving the robot. The joystick may have a spring return that automatically returns the position of the stick when released by the user. This causes the camera to be aligned with the direction of movement.

In general the robot may have a number of different mapping schemes and relative, dependent or independent, movement between the camera, the platform and drive direction. Relative movement between the camera and platform may occur in a camera based mapping scheme, a platform based mapping scheme, or some other scheme.

Although, the automatic platform rotation commands have been described as be generated by the remote station computer, it is to be understood that the robot may determine the commands and signals necessary to re-orient the platform 110 and/or the camera 38. The robot 12 may include a potentiometer (not shown) that tracks the position of the camera and provides feedback to the low level controller 80. The low level controller 80 may automatically rotate the platform to align the y-axes Yc and Yp or otherwise compensate for camera movement. The mode button 33 may allow the operator to place the system in either a tracking mode or a normal mode. In the tracking mode the robot moves relative to the camera coordinate system so that movement is intuitive relative to the screen even when the camera is panned. In normal mode the robot moves within the platform coordinate system.

Figure 6:
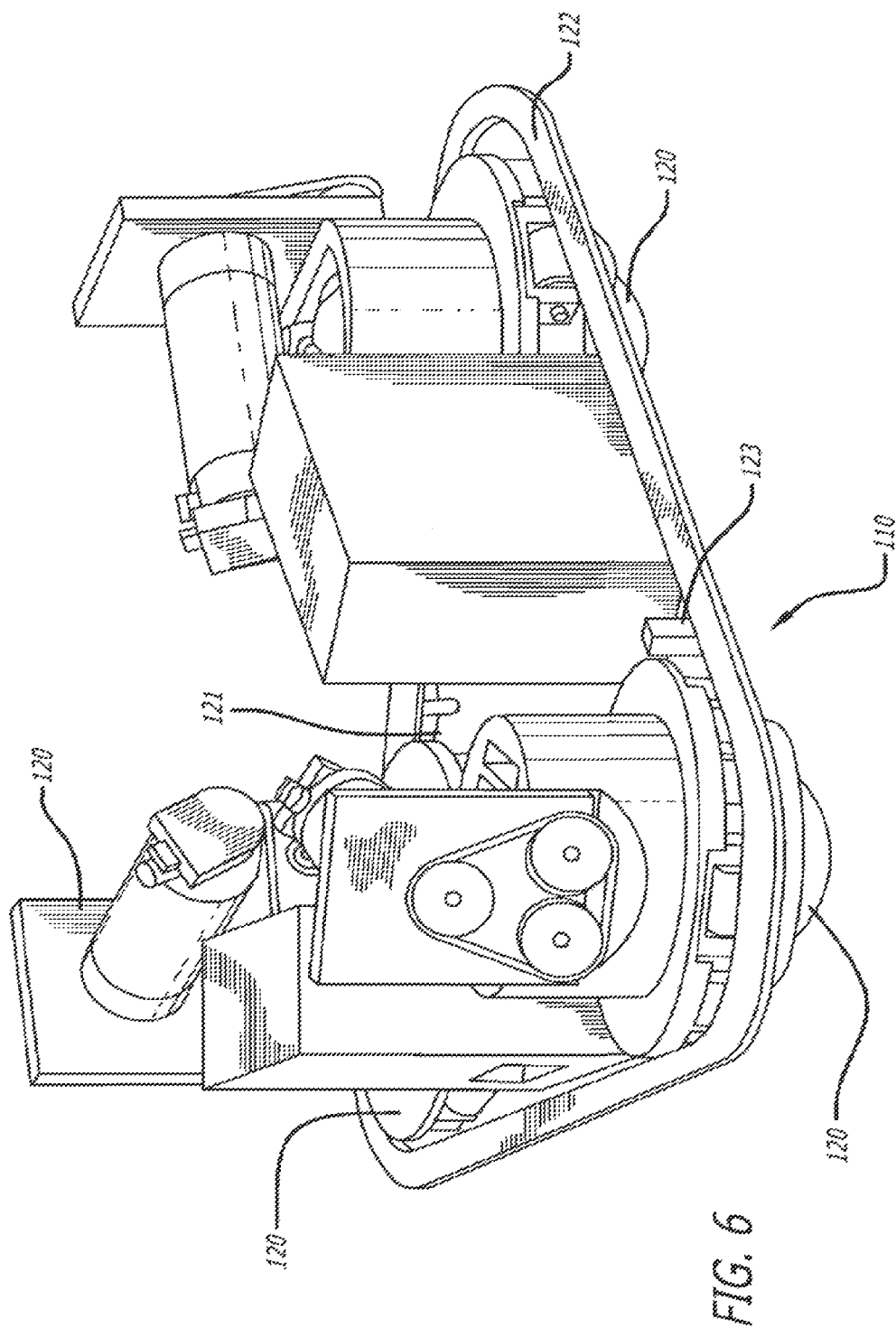
FIG. 6 is a top perspective view of a holonomic platform of the robot.

FIG. 6 shows an embodiment of a holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 7:
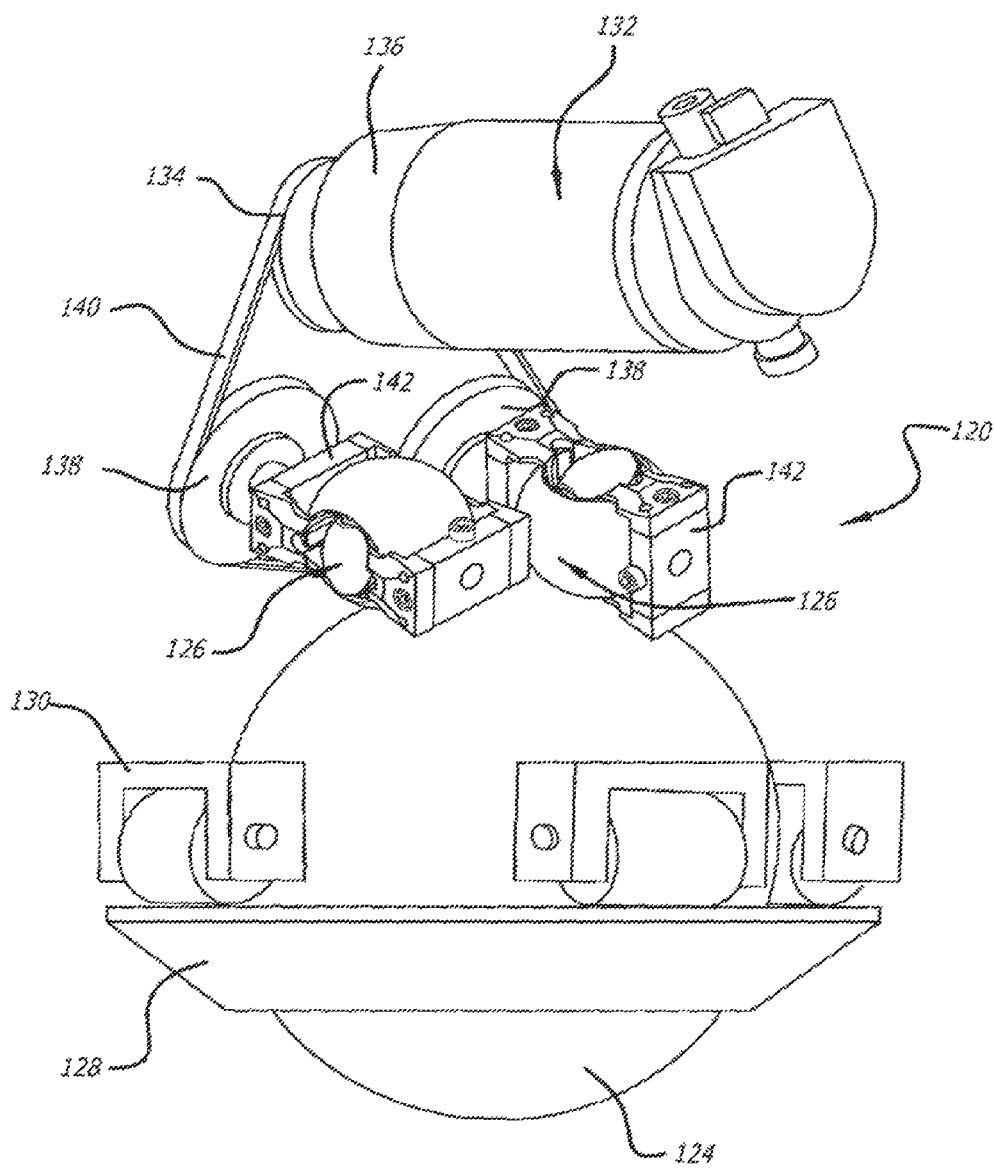
FIG. 7 is a side perspective view of a roller assembly of the holonomic platform.

FIG. 7 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin in a direction orthogonal to the drive direction when one of the other roller assemblies 120 is driving and moving the robot 12.

Figure 8:
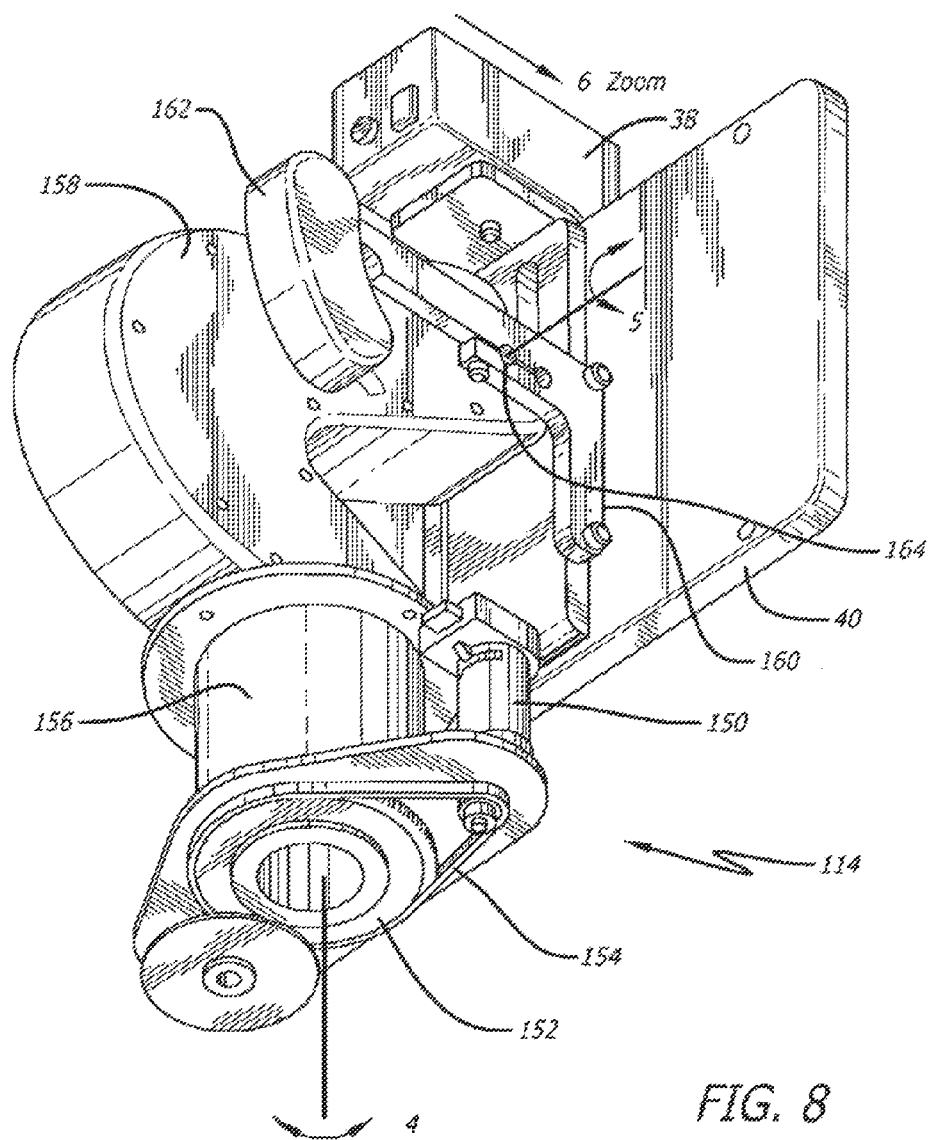
FIG. 8 is a bottom perspective view showing a pedestal assembly of the robot.

As shown in FIG. 8, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

As shown in FIG. 9, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |

TABLE II-continued

| | Requesting User | | | | |
|---|---|---|---|---|---|
| | Local | Caregiver | Doctor | Family | Service |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |

TABLE III-continued

| Control Commands | | |
|---|---|---|
| Command | Example | Description |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| Reporting Commands | | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |

TABLE IV-continued

Reporting Commands

| Command | Example | Description |
| --- | --- | --- |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A mobile robot system that is controlled through an input device, comprising:
   a robot that has a camera within a camera reference coordinate system fixed to said camera and a mobile platform with a platform reference coordinate system and a drive vector mapped to the platform reference coordinate system; and,
   an input device that causes movement of said camera and said mobile platform within the camera reference coordinate system and movement of said mobile platform along the drive vector within the platform reference coordinate system, said input device includes a mode button that allows the system to be switched between a mode wherein said mobile platform moves within the camera reference coordinate system or a mode wherein said mobile platform moves within the platform reference coordinate system.

2. The system of claim 1, wherein said input device is a joystick.

3. The system of claim 1, wherein said mobile platform rotates to align an axis of a platform reference coordinate system fixed to said mobile platform with an axis of the camera reference coordinate system.

4. The system of claim 1, wherein movement of said mobile platform is accompanied by a movement of said camera.

5. The system of claim 2, wherein twisting said joystick causes rotation of said camera and pivoting said joystick causes said mobile platform to move.

6. The system of claim 1, further comprising a computer coupled to said input device and said robot.

7. The system of claim 1, further comprising a wireless base station coupled to said robot and said input device.

8. The system of claim 7, further comprising a broadband network that is coupled to said wireless base station and said input device.

9. The system of claim 1, wherein said robot includes a monitor.

10. A mobile robot system that is controlled through an input device, comprising:
    a robot that has a camera within a camera reference coordinate system fixed to said camera, and a mobile platform with a platform reference coordinate system and a drive vector mapped to the platform reference coordinate system; and,
    input means for moving said camera and said mobile platform within the camera reference coordinate system and moving said platform along the drive vector within the platform reference coordinate system, said input means includes a mode button that allows the system to be switched between a mode wherein said mobile platform moves within the camera reference coordinate system or a mode wherein said mobile platform moves within a platform reference coordinate system.

11. The system of claim 10, wherein said input means includes a joystick.

12. The system of claim 10, wherein movement of said mobile platform is accompanied by a movement of said camera.

13. The system of claim 11, wherein twisting said joystick causes rotation of said camera and pivoting said joystick causes said mobile platform to move.

14. The system of claim 10, wherein said input means includes a computer.

15. The system of claim 10, further comprising a wireless base station coupled to said robot and said input means.

16. The system of claim 15, further comprising a broadband network that is coupled to said wireless base station and said input means.

17. The system of claim 1, wherein said robot includes a monitor.

18. A method for controlling a robot, comprising:
moving a camera of a robot within a camera reference coordinate system that is fixed to the camera;
moving the robot along a drive vector mapped to a platform reference coordinate system that is fixed to a mobile platform of the robot; and,
selecting between a mode wherein said mobile platform moves within the camera reference coordinate system or a mode wherein said mobile platform moves within a platform reference coordinate system.

19. The method of claim 18, wherein the mobile platform is rotated so that an axis of the platform reference coordinate system is aligned with an axis of the camera reference coordinate system.

20. The method of claim 18, wherein the robot receives commands from a wireless base station.

21. The method of claim 20, wherein the command is transmitted through a broadband network.

22. The method of claim 18, wherein the camera and robot are moved through manipulation of a joystick.

\* \* \* \* \*